(12) United States Patent
Chin et al.

(10) Patent No.: US 7,787,119 B2
(45) Date of Patent: Aug. 31, 2010

(54) METHOD FOR REMOTE SENSING OF TARGETS IN A TRANSPARENT MEDIUM USING ULTRA-SHORT INTENSE LASERS

(75) Inventors: See Leang Chin, Quebec (CA); Jean-François Daigle, Quebec (CA); Weiwei Liu, Tianjin (CN)

(73) Assignee: Université Laval, Québec (CA)

( * ) Notice: Subject to any disclaimer, the term of this patent is extended or adjusted under 35 U.S.C. 154(b) by 693 days.

(21) Appl. No.: 11/710,527

(22) Filed: Feb. 26, 2007

(65) Prior Publication Data

US 2008/0030727 A1   Feb. 7, 2008

Related U.S. Application Data

(63) Continuation-in-part of application No. 10/682,365, filed on Oct. 10, 2003, now Pat. No. 7,184,143.

(60) Provisional application No. 60/417,648, filed on Oct. 11, 2002.

(51) Int. Cl.
*G01J 3/30* (2006.01)
(52) U.S. Cl. .................................................... 356/318
(58) Field of Classification Search ......... 356/317–318, 356/417
See application file for complete search history.

(56) References Cited

U.S. PATENT DOCUMENTS

2008/0180655 A1* 7/2008 Bruch et al. ................. 356/318

OTHER PUBLICATIONS

Rairoux et al., "Remote sensing of the atmosphere using ultrashort laser pulses" Aug. 16, 2000, Applied Physics B, vol. 71, pp. 573-580.*
Luo et al., "Effect of beam diameter on the propagation of intense femtosecond laser pulses" Nov. 10, 2004, Applied Physics B, vol. 80, pp. 35-38.*
Luo et al., "Remote sensing of pollutants using femtosecond laser pulse fluorescence spectroscopy" Nov. 12, 2005, Applied Physics B, vol. 82, pp. 105-109.*
Kosareva et al., "Controlling a bunch of multiple filaments by means of a beam diameter" Nov. 19, 2005, Applied Physics B, vol. 82, pp. 111-122.*
Liu et al., "An efficient control of ultrashort laser filament location in air for the purpose of remote sensing" Jul. 1, 2006, Applied Physics B, vol. 85, pp. 55-58.*

* cited by examiner

*Primary Examiner*—Kara E Geisel
(74) *Attorney, Agent, or Firm*—Ogilvy Renault, LLP (57) ABSTRACT

There is described a method for identifying at least one target in a substantially transparent medium. High-power, ultra-short laser pulses are transmitted into the medium. A diameter of the laser pulses is enlarged and the laser pulses having an enlarged beam diameter are focused using a focusing element so as to generate filaments substantially near a geometrical focal zone of the focusing element, whereby a spontaneous fluorescence signal (amplified through amplified spontaneous emission or not) is detected and analyzed to identify the target.

19 Claims, 10 Drawing Sheets

METHOD FOR REMOTE SENSING OF TARGETS IN A TRANSPARENT MEDIUM USING ULTRA-SHORT INTENSE LASERS

CROSS-REFERENCE TO RELATED APPLICATIONS

The present application is a continuation-in-part of U.S. patent application Ser. No. 10/682,365, filed on Oct. 10, 2003 now U.S. Pat. No. 7,184,143, which claims priority of U.S. provisional application No. 60/417,648, filed on Oct. 11, 2002.

FIELD OF THE INVENTION

The invention relates to the field of Light Detecting and Ranging (LIDAR). More specifically, it relates to identifying targets in a transparent medium such as air using a LIDAR system.

BACKGROUND OF THE INVENTION

Filaments over distances up to several kilometers are formed when high-power ultra-short laser pulses are launched in air. They are created by a dynamic interplay between two nonlinear effects, i.e. Kerr self-focusing and subsequent plasma defocusing. Self-phase modulation and self-steepening of the pulse give rise to a strong broadening of the spectrum. The consequence is a white light laser pulse (super continuum). Potential practical applications of these phenomena include lightning discharge control and remote sensing.

It is known in the art to combine LIDAR (Light Detection and Ranging) techniques and time-resolved absorption spectroscopy techniques and apply them to a pulsed broadband light source in order to perform range-resolved multi-trace analyses simultaneously. While this process can be applied to the remote sensing of pollutants in the atmosphere, sensitivity is an issue. Normally, for detecting different pollutant molecules, different lasers with different output wavelengths are required. This causes difficulties especially for the analysis of multi-component mixtures.

There is a need to develop a new scheme of LIDAR technique to detect pollutant molecules in air, or any other transparent medium, with improved sensitivity.

SUMMARY OF THE INVENTION

Accordingly, an object of the present invention is to determine the composition of a transparent medium such as air or water using an efficient and simple remote sensing method.

It is also an object of the present invention to observe an amplification of an emitted signal in order to increase sensitivity in the remote sensing of molecules.

According to a first broad aspect of the present invention, there is provided a method for identifying at least one molecule in a substantially transparent medium, the method comprising: transmitting high-power, ultra-short laser pulses into the medium so as to generate filaments in which a spontaneous fluorescence signal propagating along an axis of the filament is amplified by stimulated emission; detecting the amplified spontaneous fluorescence signal; and analyzing the florescence signal to identify said molecule.

Preferably, the amplified spontaneous fluorescence signals are detected in a direction opposite that of the transmitted laser pulses and the detector is gated. Also preferably, transmitting comprises transmitting femtosecond laser pulses and transmitting is done using a terawatt femtosecond Ti-sapphire laser system.

Additionally, by using trigger-and-delay electronics, a fluorescence spectrum of the signal can be acquired at any given time corresponding to the sum of travel time of the laser to a given point in space and the travel time of the fluorescence signal from the point in space to the detector. By varying the delay between the firing of the laser and the acquisition of the spectrum, information on the composition of the medium as a function of the distance from the laser can be obtained.

In accordance with a second broad aspect of the present invention, there is provided a method for identifying at least one target in a substantially transparent medium, the method comprising: transmitting high-power, ultra-short laser pulses into the medium, enlarging a diameter of the laser pulses, and focusing the laser pulses having an enlarged beam diameter using a focusing element so as to generate filaments substantially near a geometrical focal zone of the focusing element; detecting a spontaneous fluorescence signal; and analyzing the florescence signal to identify the target.

In accordance with a third broad aspect of the present invention, there is provided a system for remote detection of at least one target in a substantially transparent medium, the system comprising: a laser system for transmitting high-power, ultra-short laser pulses into the medium; an optical element for enlarging a beam diameter of the laser pulses; a focusing element for focusing the laser pulses having an enlarged beam diameter so as to generate filaments substantially near a geometrical focal zone of the focusing element; and a detection system for detecting a spontaneous fluorescence signal in one of a forward and a backward direction.

The target could be molecules, atoms, aerosols, powders or solids.

BRIEF DESCRIPTION OF THE DRAWINGS

These and other features, aspects and advantages of the present invention will become better understood with regard to the following description and accompanying drawings wherein.

DETAILED DESCRIPTION

When high-power ultra-short (femtosecond) laser pulses are launched in air, they self-transform into streaks of filaments over distances up to several km. That is to say, multiple filaments of shorter lengths are substantially aligned in a non-continuous manner over distances up to several km. Although multiple filaments are common, it is not impossible that a single filament be created. These filaments are the result of a dynamic balance between two nonlinear effects. The first is self-focusing of a laser pulse due to the Kerr effect in the atmosphere. The beam focuses by itself, resulting in a small beam diameter and hence high peak intensity. At that self-focal region, the high intensity laser pulse induces multiphoton/tunnel ionization (MPI) of the gas molecules in air. This results in the weak plasma in the self-focal region, whose density is low (about $10^{15}/cm^3$) compared with the density of one atmosphere of air ($3 \times 10^{19}/cm^3$). The second balancing effect is the defocusing of the laser pulse in the weak plasma created in the self-focal region. The laser peak intensity in the filaments in air is clamped down to about $5 \times 10^{13}$ W/cm$^2$. At this intensity, most molecules will undergo MPI and fragmentation. Many of the ionization and fragmentation are expected to fluoresce with distinguishable molecular spectra due to the different nonlinear interaction between the molecules and the intense femtosecond laser fields. This nonlinear fluorescence created in the filament is a new physical phenomenon and is strongly emitted along the forward and backward directions. Since every molecule has its particular feature in the fluorescence spectrum, these fluorescence spectra can be made use of as the fingerprint patterns for pollution measurement using the LIDAR technique.

The white light laser pulse (super continuum) combined with linear absorption spectroscopy technique has been used for atmospheric remote sensing. A terawatt femtosecond Ti-sapphire laser system mounted on a mobile unit, teramobile, was recently built to carry out long-range propagation experiments in air and LIDAR type of measurements in the atmosphere.

Figure 1:
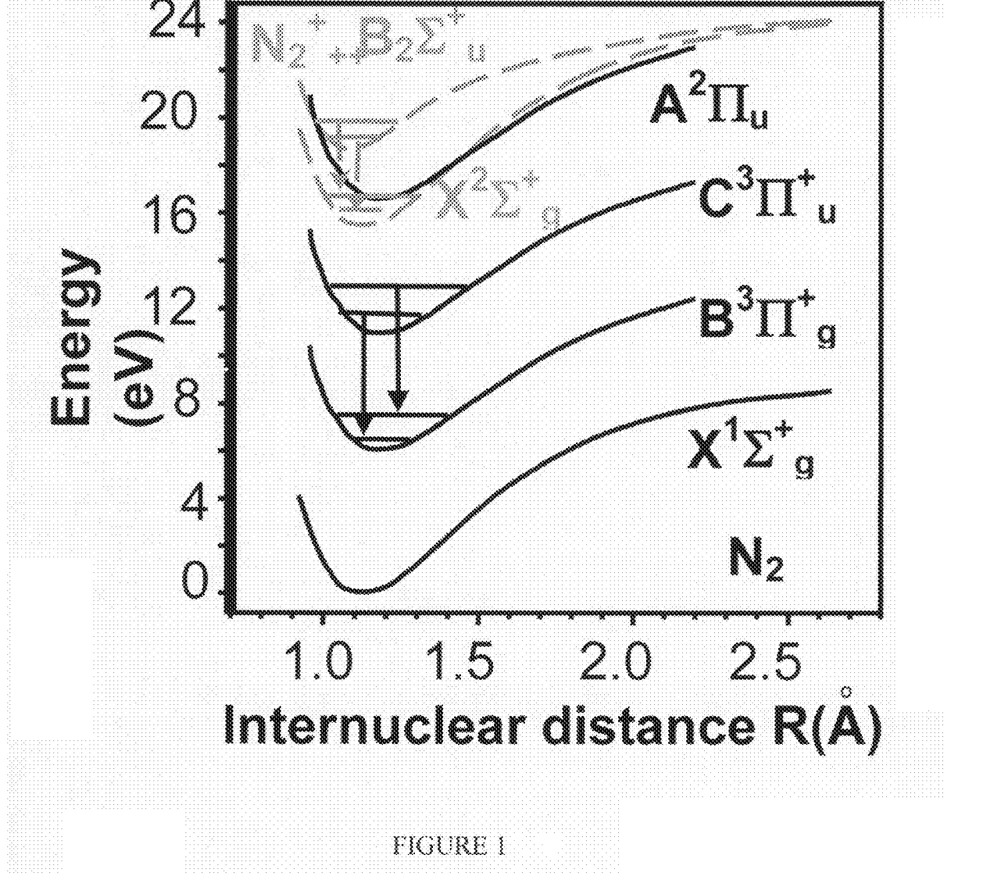
FIG. 1 is the potential energy curve for $N_2$ and $N_2^+$.

In air, so-called clean fluorescence of nitrogen molecules and ions are observed from the filaments; i.e. the contribution of the super continuum is quite low compared with that from the optical break down measured with long pulses. The spectra are assigned to the first negative band of $N_2^+$ ($B^2\Sigma_u^+ \rightarrow X^2\Sigma_g^-$) and the second positive band of $N_2$ ($C^3\pi_u \rightarrow B^3\pi_g$). We have proven that nitrogen molecules inside the filament are first ionized, some of them into the excited ionic state through the ejection of an inner valence electron. Subsequent radiative decay of the excited ion gives rise to the first negative band (See FIG. 1). Electron-ion recombination and collision lead to the emission of the second positive band. We investigated the fluorescence from inside the filaments generated by a femtosecond Ti-sapphire laser pulse in air. The angular distribution and intensity dependence of the signal show clear evidences of amplified spontaneous emission (ASE).

Strictly speaking, a filament is the weak plasma column left behind by the continuous series of self-foci of the laser pulse. The laser peak intensity inside the series of foci is clamped down to about $5 \times 10^{13}$ W/cm$^2$ in air.

The high power femtosecond laser system consists of a Ti:Sapphire oscillator (Spectra Physics Maitai) followed by a regenerative (Spectra Physics Spitfire) and a two-pass Ti:Sapphire amplifiers. The amplified beam is sent to a portable compressor that can be moved close to the experimental setup. The pulse duration at the output of the compressor is 42 fs measured by a single-shot autocorrelator and the central wavelength is 810 nm with a bandwidth of 23 nm (FWHM). The maximum output energy is about 20 mJ per pulse with the repetition rate of 10 Hz.

Figure 2:
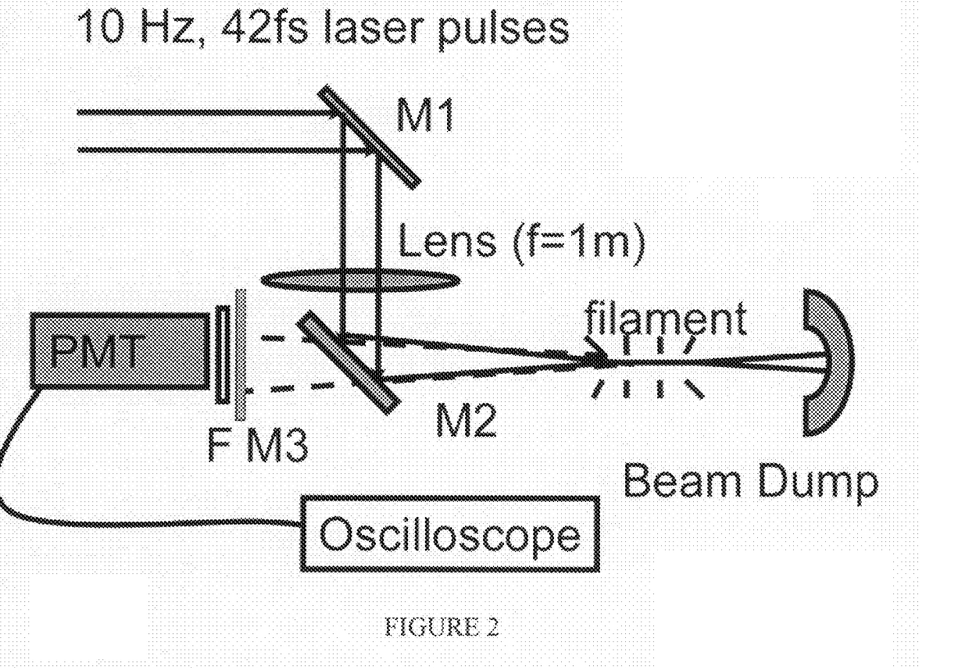
FIG. 2 is the setup used as an experimental setup.

The experimental setup is shown in FIG. 2(a) for analyzing fluorescence emission amplified by stimulated emission in a direction of the axis of the filament. The laser beam is firstly focused with an f=100 cm lens. A dielectric mirror (diameter=2.54 cm) having high reflectivity around 800 nm while transmitting UV light is put just after the lens to reflect the beam at a 45° incident angle. In the forward direction of the laser, filaments are generated before the geometrical focus. A beam dump blocks the laser beam just before the wall of the lab. The amplified fluorescence from air is detected using a photo multiplied tube (PMT) (Hamamatsu R74000U) which is put behind the last mirror facing the direction of the beam. An iris (5 mm diameter) is put in front of the PMT to limit the field of view. The fluorescence is selected by an appropriate interference filter with 10 nm bandwidth around the detected wavelength together with a high reflectivity dielectric coated fused silica mirror (reflectivity: 99%, central wavelength: 800; bandwidth: around 100 nm) a broad band filter in 800 nm for cutting off scattered laser light. The fluorescence studied includes (1-0) transition of the second positive band system of $N_2$ ($C^3\pi_u$-$B^3\pi_g$ transition) at 357 nm and the band head of the first negative band system of $N_2^+$ ($B^2\Sigma_u^+$-$X^2\Sigma_g^-$ transition) at 391 nm.

The experiment is also done without focusing lens. In this case, filaments are generated only due to self-focusing. The distance between the exit of compressor and the beam dump is about 13.5 m. Since the filament is far away from the detector, the fluorescence signals are much weaker than that in the focusing geometry. We use a UV filter to cut the light above 400 nm instead of using an interference filter to obtain more dynamic range for the signal. Thus the fluorescence signal from $N_2$ molecules and ions are all measured.

When the intense laser beam is focused by an external focusing lens, the filament will start before the geometrical focus and the filament length will increase towards the focusing lens with increasing laser energy. The intensity of the amplified fluorescence is found to increase nonlinearly with increasing pump laser energy. The latter is converted into filament length defined approximately as the distance between the geometrical focus and the position of the self-focus of the peak of the pulse (see below for more precision). Without external focusing lens, a parallel beam with a Gaussian beam profile will self-focus at:

$$z_f = \frac{0.367ka^2}{\left\{\left[\left(\frac{P}{P_{crit}}\right)^{1/2} - 0.852\right]^2 - 0.0219\right\}^{1/2}} \quad (1)$$

Here $ka^2$ indicates the diffraction length, where k is the wave number and a is the radius at $1/e^2$ level of the beam profile. In our experiment, the radius of the beam is around 5 mm. The critical power for self-focusing is:

$$P_{crit} = \frac{3.77\lambda^2}{8\pi n_0 n_2}$$

where $\lambda$ is the laser wavelength, $n_0$ and $n_2$ characterize the intensity dependent refractive indices $n=n_0+n_2 I$, where I is the laser intensity. In air, the critical power for self-focusing is 3

GW. In the case of external focusing using a lens of focal length f the position of the self-focus will change to:

$$z'_f = \frac{z_f f}{z_f + f} \quad (2)$$

The filament length is L=f-$z_f$. Any refocusing after the geometrical focus is neglected because the intensity would be weaker in the re-focusing zone and hence the fluorescence signal is weaker and is neglected as an approximation. The intensity of the fluorescence signal from $N_2$ at 357 nm collected by the fused silica lens versus the filament length is plotted in FIG. 3.

Figure 3:
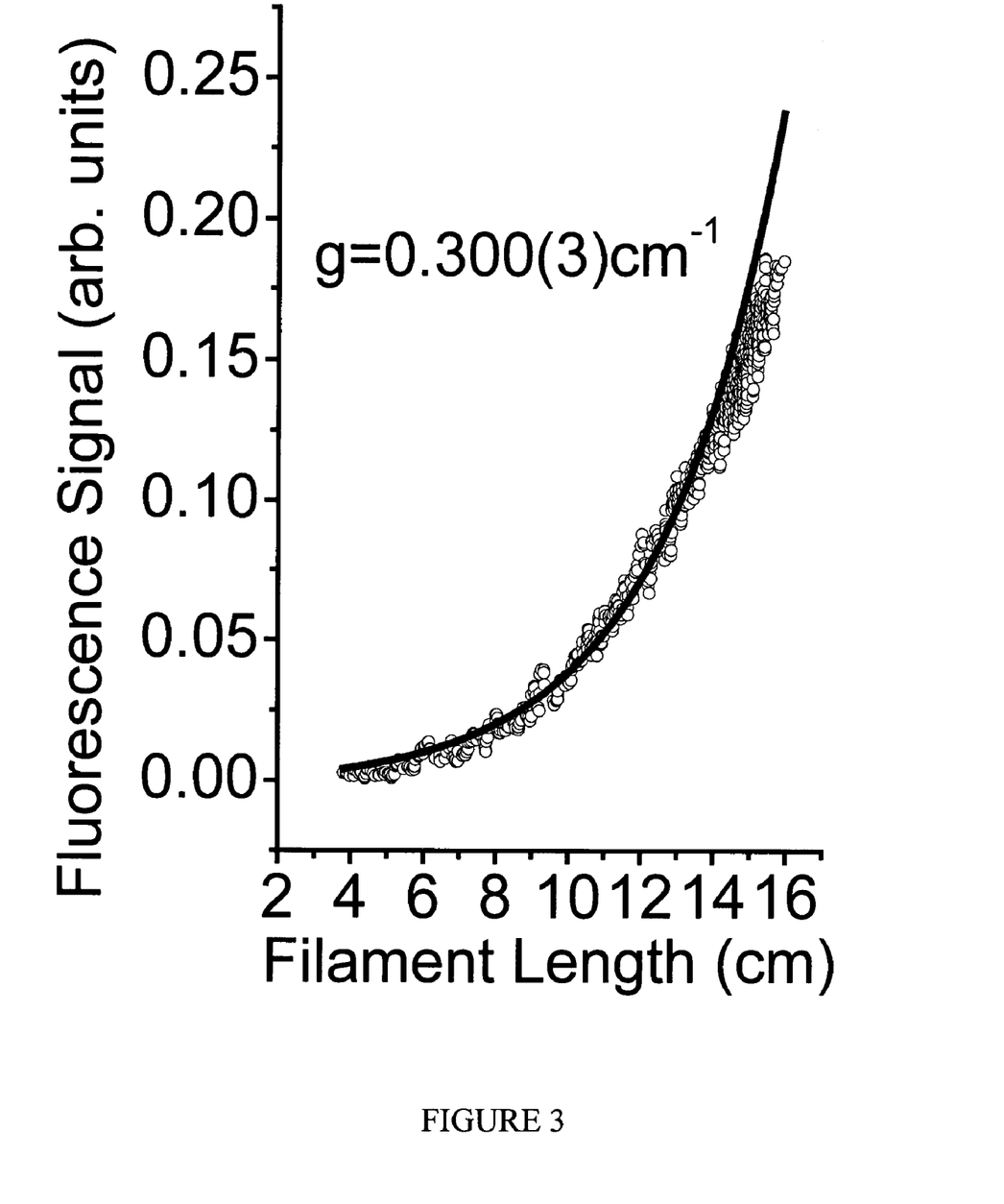
FIG. 3 is a graph of the fluorescence intensity of $N_2$ at 357 nm versus the filament length.

Consider the filament as a long slender line source emitting fluorescence and any small length as a point source, the spontaneous emission power going out into all directions from this point source is identical. Assuming that spontaneous emission occurs uniformly along the filament, the signal we detect in PMT for ASE is given by:

$$I \propto P = \int_0^L P_s e^{gl} dl + \text{Const.} = \frac{P_s}{g}(e^{gL} - 1). \quad (3)$$

$$= \begin{cases} \frac{P_s}{g}(e^{gL} - 1) & \text{(with amplification)} \quad (a) \\ \frac{P_s}{g} \cdot gL = P_s L & \text{(without amplification } g \to 0) \quad (b) \end{cases}$$

where $P_s$ is the spontaneous emission power per unit length which goes back along the filament, g is the optical gain coefficient, L is the filament length. In the case without amplification the total signal we detected is the sum of the emission power going into a certain solid angle from all the point sources along the filament. The total signal should thus be proportional to the filament length. However, the plot in FIG. 3 shows an exponential increase in the fluorescence signal with the filament length. This is a direct indication of the existence of gain. As shown in the FIG. 3, a calculated gain curve (solid line) by using $P_s$ and g as fitting parameters fits very well the measured data with a gain coefficient of 0.305 cm$^{-1}$. For the longer filament length, the experiment data are lower than that of calculated gain which is due to the saturation effect.

The fluorescence from the first negative band system of $N_2^+$ ($B^2\Sigma_u^+$-$X^2\Sigma_g^-$ transition) at 391 nm are also studied. The fluorescence signal shows a similar tendency of exponential increase with filament length. It means the fluorescence from ions is also amplified. The gain coefficient is 0.34 cm$^{-1}$.

Figure 4:
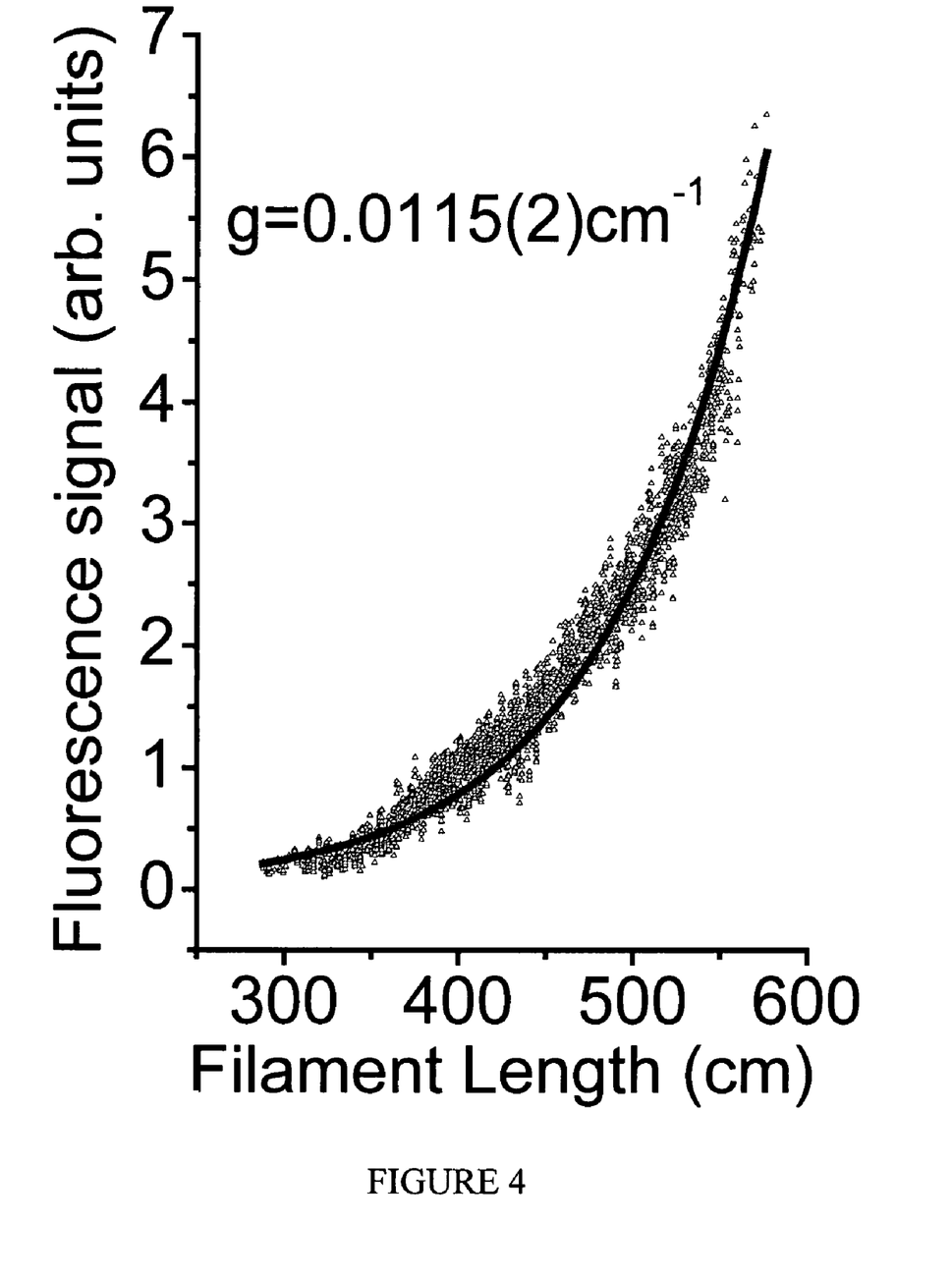
FIG. 4 is a graph of the fluorescence intensity of N2 at 357 nm versus the filament length when the laser beam propagates in air without external focusing lens.

To study the long-distance case, we measured the intensity dependence of the fluorescence emission amplified by stimulated emission in a direction of the axis of the filament generated during the laser pulse free propagation in air. In this case, the laser beam is sent to air without any focusing lenses and the filaments are generated only due to self-focus. The starting point moves towards the compressor and the filament becomes longer as the input laser energy increases. The filament length is limited by the confine of the lab. In this measurement, the filament length is determined by taking the distance between the beginning of the self-focusing point and the wall of the lab, i.e. L=1350-$z_f^1$ (cm). As we showed above, the fluorescence from both the neutral molecules and ions shows the existence of gain. Thus we expect that the signal in this measurement will show gain also. FIG. 4 is the plot for the fluorescence signal from nitrogen versus the filament length. The curve shows a similar tendency as that taken with an external focusing lens. The solid line shown in the figure is the fitting curve using Eq. 4(a). The gain coefficient is around 0.0116 cm$^{-1}$.

When the $N_2$ molecules interact with the intense ultra fast field, the molecules will first go through multiple photon ionization. An inner-valence electron is ionized resulting in an electronically excited molecular ion. The recombination of the electrons and the ions in excited states generate the $N_2$ molecules in the continuum. The $N_2$ molecules will relax from the continuum down to electronic states. When the molecules go through radiative excited state, the fluorescence is emitted. Since the population of the states is created from the higher states, the inverse population is established between the upper state and lower state. In our case, they are $C^3\pi_u$ and $B^3\pi_g$ state.

In fact, the transition we studied here is the operation wavelength of $N_2$ laser.

However, the gain length is expected to be related to the fluorescence lifetime around several ns. The relative short lifetime of the upper state means that the inversion can only be obtained during the effective lifetimes of the C-state. To estimate the lifetime of the upper state in our current experimental condition, the temporal profile of the fluorescence signal is measured with PMT by collecting the fluorescence signal in the right angle. By comparing with the measurement for the laser scattering, it is found that the lifetime of $C^3\pi_u$ is around several ns. In the experiment with an external lens to focus the laser beam, the maximum filament length is around 20 cm which corresponds to less than 1 ns traveling time for the light. When the fluorescence goes through the filament, most of the excited $N_2$ molecules remain in the upper state and the inverse population remains between the $C^3\pi_u$ and $B^3\pi_g$ states. Thus the spontaneous emission is amplified. When the laser pulses propagate in air without passing through any focusing lens, the filament length is rather long (about several meters). The effective amplification is reduced and this is what we have observed. On the other hand, the experimental and theoretical results showed the intensity distribution along the filaments oscillates gradually because of the repetitive Kerr focusing and plasma defocusing effects that lead to a dynamic balance resulting in the perceived filament. This will also result in the effective gain effect reductions since the nonlinear fluorescence is highly related to the intensity inside the filament.

It is interesting to note that our observation shows that there is gain inside the emission from the $N_2$ ions. This is probably because the electron-ion recombination rate for the upper state $B^2\Sigma_u^+$ is slower than that for $X^2\Sigma_g^-$ state resulting in a population inversion between these two states.

The exponential variation of the fluorescence from $N_2$ molecules and ions with increasing filament length indicate the fluorescence has been amplified when propagating along the filament. Since the gain length is changed with different experimental setup, the gain coefficient is different from case to case. It is expected that in the forward direction, because of symmetry, the nitrogen fluorescence would also exhibit ASE type of gain. Thus, we can say that there is laser action in the filaments generated by an intense femtosecond Ti-sapphire laser pulse in air.

The existence of gain is particularly important for remote sensing application with intense ultra fast laser. It is expected that the fluorescence from other molecules will undergo amplification during propagating along the filament as well because the molecules would be ionized first through MPI and then decay through all allowed excited states after e-ion recombination. Those radiated excited states are inverted with respect to the lower states since they are populated from the continuum down. Therefore in the direction opposite to that of the transmitted pulse, the fluorescence will be much stronger than the other directions: thus a higher sensitivity is expected. Indeed, this is a universal phenomenon in all gases which exhibit fluorescence in the filament of an intense femtosecond laser pulse.

A feasibility study was carried out on measuring the fluorescence spectra of atmospheric pollutants in our laboratory environment. The samples we chose include the following molecules: $N_2$, CO, $CO_2$, Ethylene, 1-Butene and N-Butane. All molecular spectra are free of the interference of plasma continuum because the plasma density is very low in the filament, resulting that the peaks in the spectrum are clearly resolved. Even for molecules with similar structures (such as CO and $CO_2$ or 1-Butene and N-Butane), the spectra clearly showed us the difference either on the peak positions or the intensity ratio between different peaks. This is due to the different nonlinear interactions between those molecules and the laser pulses. The minimum detection sensitivity of this technique was also evaluated by measuring the characteristic spectra from the mixture of these gases with air at different partial pressures. The sensitivity of this technique could reach several tens to several hundreds of ppb (parts per billion) level in volume concentration.

The feasibility of detecting fluorescence at a long distance was checked by measuring one of the fluorescence lines from $N_2$ in air using the LIDAR technique as well. We are able to detect the signal from many tens of meters away. Were it not for the confine of the laboratory, this distance can still be much longer. This proves that long distance fluorescence is measurable.

In order to measure a signal over a desired time interval corresponding to a desired range, a shutter is used on the detector. The shutter is set to open after a fixed amount of time, for example 500 ns. In order to obtain a signal received between 500 ns and 700 ns, the spectra of the signal captured after 500 ns and the spectra of a signal captured after 700 ns are subtracted from one another in order to obtain a spectra for a signal from 500 ns to 700 ns. This can be done using a gated detector.

It is also possible to detect the amplified spontaneous fluorescence signals in the same direction as that of the transmitted pulse by placing a detector in front of the source. In this case, the detector senses the amplified spontaneous fluorescence signals that are maintained in the waveguide formed by the filament and are moving forward. There is a possibility that the source burns a hole through the detector when the detector is placed on a same axis as the source and receives forward moving amplification signals because it also receives the original femtosecond pulse output from the source. Therefore, it may be necessary to replace the detector after a certain amount of transmissions and detections. Receiving optics can be designed to reduce the damage to the detector. Such receiving optics are known to a person skilled in the art.

When we need to increase the return signals from a remote target excited by the filaments of a laser pulse, the energy of the pulse is increased to enhance the excitation. However, linear scaling does not work well. The femtosecond laser pulse, once its energy is increased, will have some hot zones across its spatial cross section. These hot zones will each tend to self-focus into a filament. This is the phenomenon of multiple filamentation. Normally, such pulses emitted from an amplifier have relatively large diameters so as to avoid damage to the gratings in the pulse compressor. Multiple filaments that result from such relatively large diameter pulses will compete for the energy inside the limited reservoir of the pulse leading to many low plasma density structures inefficient for remote sensing purposes. In fact, it is now recognized that filament competition will lead to random and relatively weak return signal from the target because of this phenomenon of filament competition.

A technique to avoid or minimize this competition is to reduce the diameter of the beam such that when they self focus, the various hot zones will 'cooperate' and the electric field distribution of and around each filament will undergo constructive interference with the others. This interference occurs because the filaments' zones are now very close to one another. This idea was indeed proven valid and the signal was increased by more than three orders of magnitude by reducing the laser pulse's diameter by about three times. However, in this case, filamentation started rather early and the self-focusing position could not be changed naturally by increasing the negative chirp or the beam divergence. This is because when the laser beam diameter is 'squeezed' down, the hot zones' diameters are also reduced and forced together around the beam center. According to eq. (1), a smaller diameter hot zone would lead to a shorter self-focal distance which results in early filamentation at short distances making remote detection a hard task.

There is provided herewith a device to move the filament zone by using the combination of beam expansion and geometrical focusing, as described in [W. Liu, F. Theberge, J.-F. Daigle, P. T. Simard, S. M. Sarifi, Y. Kamali, H. L. Xu, S. L. Chin, *An efficient control of ultrashort laser filament location in air for the purpose of remote sensing*, Applied Physics B, 85, 55 (2006)], which is hereby incorporated by reference. From eq. (1), when the beam is expanded, the diameter/size of the hot zone in the beam cross section becomes larger which in turn, increases the self-focusing distance. The beam diameter could in principle be made very large; hence, the self-focusing distance of each hot zone could become very far. We now use a focusing element to force the beam energy to converge towards the geometrical focus. The focal distance of the device is made shorter than the hot zones' self-focusing distance. Thus, the combination of self-focusing and geometrical focusing will bring the self-focal zones (filaments) to the position in front of or right next to the geometrical focal zone or the Rayleigh range. This is equivalent to squeezing the beam diameter in front of the geometrical focal region to enhance constructive interference among the various filaments. This high intensity zone will then strongly interact with any medium to create a plasma and fluorescence signals.

A beam device based upon the above principle is designed to execute remote detection measurements. The device consists of a 5 cm diameter convex mirror, whose focal length is −50 cm, and a focusing lens with focal length of 100 cm (diameter of 8 cm). The focusing lens was installed on a computer-controlled motorized stage, allowing us to change the effective focal length of the device. The purpose of the device is to generate high plasma density filaments at a far distance with a minimum of white light. In order to counter the unwanted effects of multi filamentation energy competition, the hot spots are stretched by increasing the beam diameter with the convex mirror. Moreover, based on equation (1), a larger beam diameter leads to an increased self focusing distance that contributes to the generation of high plasma density filaments. From equation (2), if $z_f$ is much larger than f, the self focusing position $z_f^i$ is approximately equal to f. This means that all the energy contained inside the filaments are merged around the geometrical focusing area.

The design of such a beam sending device is not a trivial solution for anybody working with remote sensing. In fact, from the linear optics theory, because of diffraction, it is impossible to deliver high laser intensity at far distances. As an example, let us consider an ideal aberration-free beam sending device, the diameter of the focal area obtained from 'linear' laser light focused at 1000 m is approximately 1 cm. Because of this limitation, the delivered intensity decreases considerably as a function of distance, reducing the chances of obtaining efficient remote detection. On the other hand, the clamped intensity of filaments generated by terawatt laser pulses is constant at any distance and circumvents this limitation. In fact, in our design, even if the self focusing distance is longer than the geometrical focus, the non linear effects still occur leading to a beam sending device which is not diffraction limited.

In order to demonstrate its efficiency, our beam sending device was used for remote detection in a contaminated aqueous cloud of micron size aerosols. The experiments were performed with the setup shown in FIG. 6. Laser pulses, centered at 800 nm, emitted with a 10 Hz repetition rate were focused, using our special device into an aerosol cloud located at various distances. The beam sending device sends the filaments to the aerosol cloud located in a distant chamber. The spectra are collected using a LIDAR and analyzed by a grating spectrometer. The chamber is located at 5 m, 20 m, 50 m and 70 m from the LIDAR mirror.

Aerosols were generated by using a commercial ultrasonic humidifier and injected in a mobile aerosol chamber. The aqueous solution is made from a de-ionized water solvent in which the appropriate quantity of the different tested salts ($PbCl_2$, $FeCl_2$, $CuCl_2$, NaCl) is added.

The 61 cm×61 cm×120 cm aluminum aerosol chamber is designed in the following way. Two circular apertures of 10 cm diameter were made on two opposite sides of the chamber to allow the laser pulses in and out of the interaction volume. The aerosols traveled from the humidifier to the interior of the chamber via a flexible tube. The aerosol droplets, due to gravity, tend to accumulate on the chamber's lower area. In order to counter this unwanted behavior and obtain a quasi-uniform and near constant aerosol distribution throughout the chamber's volume, an 8 cm diameter ventilator, positioned on the bottom surface of the chamber, blows the falling aerosol droplets in the upward direction. This ensures that the laser pulse interacts over 120 cm with a thin, practically homogeneous aerosol fog. Under these conditions, the cloud's optical density is characterized by 95% transmission of a 15 mW continuous wave He—Ne laser at 632 nm. Such a low fog density was selected so as to reproduce real natural clouds and demonstrate the practical sensitivity of the technique. As a matter of fact, this transmission of the 632 nm wavelength roughly corresponds to a droplet concentration of 300 $cm^{-3}$ which is approximately 3 times the concentration of the thinnest natural clouds. At all times, in order to avoid laboratory contamination, a flexible plastic pipe connects the chamber to the building's ventilation system and sucks the aerosol to the outdoors. The negative pressure inside the chamber prevented the exceeding aerosol from escaping the chamber into the laboratory. Since some of the materials are rather toxic ($PbCl_2$) or corrosive ($FeCl_2$), the ventilation suction was maximized to eliminate any risks to human and environment health.

In the experiment, beside the focusing device, a typical fiber coupled LIDAR setup collected the fluorescence spectra. The signal was delivered to a SpectraPro-500i SP-558 spectrometer equipped with a PIMAX:512 ICCD camera. The grating's groove density is 1200/mm and the slit width is 100 μm. For each experimental condition, the fluorescence signals were optimized by adjusting the effective focal length of the sending device.

The spectrum presented in FIG. 7 is the result of 160 shots accumulation. The corresponding laser pulse duration was negatively chirped to 500 fs with 51 mJ compressed pulse energy. The de-ionized water solution contained $FeCl_2$, $PbCl_2$, $CuCl_2$ and NaCl at respective concentrations of 0.018 $mol/L_{water}$, 0.0003 $mol/L_{water}$, 0.004 $mol/L_{water}$ and 0.009 $mol/L_{water}$. The distance from the chamber's entrance was 3.5 m and 5.0 m to the focusing component of the sending device and the LIDAR mirror, respectively. The gate of the ICCD camera was opened for 1 ms, 5 ns after the laser pulse had arrived at the cloud layer. In addition to the strong fluorescence detected from Cu I, Fe I and Pb I lines in the range from 300 nm to 700 nm, the main atomic hydrogen fluorescence bands of the Balmer series were observed. The existence of hydrogen lines indicates that the water droplets have been exploded due to ionization and recombination of the plasma. The constituent ionic elements inside the droplet were thus created and through electron-ion recombination, their neutral fluorescing states were formed.

In FIGS. **8*a*, 8*b*, 8*c*, the regions A, B and C shown in FIG. 7 are enlarged. Regions A and C clearly show that, when these four salts are mixed together, Cu I and Na I emissions can easily be distinguished from the background and from the other materials. FIG. 8*b*** shows the selected region for Fe I and Pb I. Three Fe I and one Pb I peaks are observed. It is clear that under these conditions, both systems can be distinguished even if the spectral spacing between Pb I 405.68 nm and Fe I 406.35 nm is less than a nanometer.

The different detection limits of the various compounds are measured using 500 fs negatively chirped pulses of 51 mJ energy launched towards the cloud. The fog concentration is, once again, characterized over 120 cm with a 95% transmission of the 632 nm He—Ne laser light. The characterizations were accomplished with respect to the 324.75 nm, 404.58 nm, 405.68 nm and 589 nm atomic transitions for Cu, Fe, Pb and Na respectively. For each salt, the solution was prepared individually and the concentration was varied and plotted against the signal intensity for a given line. Because the plotted curves behaved linearly, we could find the detection limit of the method for the various compounds using a linear extrapolation to the 3σ level (where σ is the standard deviation of the signal). FIG. 9 is an example of such plots for Pb. The detection limits were respectively, for $FeCl_2$, $CuCl_2$, $PbCl_2$ and NaCl [25], 0.001 $mol/L_{water}$ (127 $mg/L_{water}$), 0.0002 $mol/L_{water}$ (27 $mg/L_{water}$), 0.00003 $mol/L_{water}$ (9 $mg/L_{water}$) and 0.00005 $mol/L_{water}$ (3 $mg/L_{water}$). For these thin fog conditions, the detection limit for lead is the lowest. The droplet concentration is 300 $cm^{-3}$, and the 500 fs negatively chirped pulses have 51 mJ energy.

However, all these values represent the quantity of salt contained in the water solution. In fact, from the 95% transmission of the 632 nm wavelength, we calculated an approximate droplet concentration of 300 $cm^{-3}$. The rest of the volume is totally occupied by air at STP. As a consequence, laser pulses will interact with a medium consisting of air and water spheres containing high density contaminants. According to the 'US environmental protection agency' (NAAQS, National Ambient Air Agency, see http://www.epa.gov/air/criteria.html), the tolerated standard concentration for respiratory exposure to airborne substances containing lead is 1.5 $\mu g_{pb}/m_{air}^3$. Let us consider our situation in which lead is found in liquid $H_2O$ containing $PbCl_2$ at the limiting concentration of our detection. Under these conditions, the 5 μm radius droplet contains $16\times10^{-20}$ moles of lead dichloride. With a droplet density of 300 000 $L^{-1}$ of air, the lead concentration is approximately 14 $ng/m_{air}^3$. This is two orders of magnitude lower than the tolerated standard concentration cited above. Thus, we can conclude that the current technique could be efficiently used to detect such pollutants (lead) in industries and in other contaminated sites so as to prevent many unnecessary short and long term accidents causing respiratory intoxication.

Due to the technique's high sensitivity, long distance experiments were performed in a corridor next to the laboratory. Since the fluorescence signals originating from the various constituents diluted in the droplets had a similar intensity, only sodium was used in these experiments. Three different chamber positions were done: 20 m, 50 m and 70 m from the LIDAR mirror. A 5 g/L salt solution was used. In order to avoid early filamentation in the 10 m tube linking the corridor to the laboratory, negatively chirped 10 ps/72 mJ pulses were launched. Due to limited corridor distance, it was discovered that, even at 70 m, the signal is still above the 3σ limit and the lines are easily distinguished from the background. In principle, based upon the current design of the device, it is possible to generate intense filaments at km range.

Figure 10:
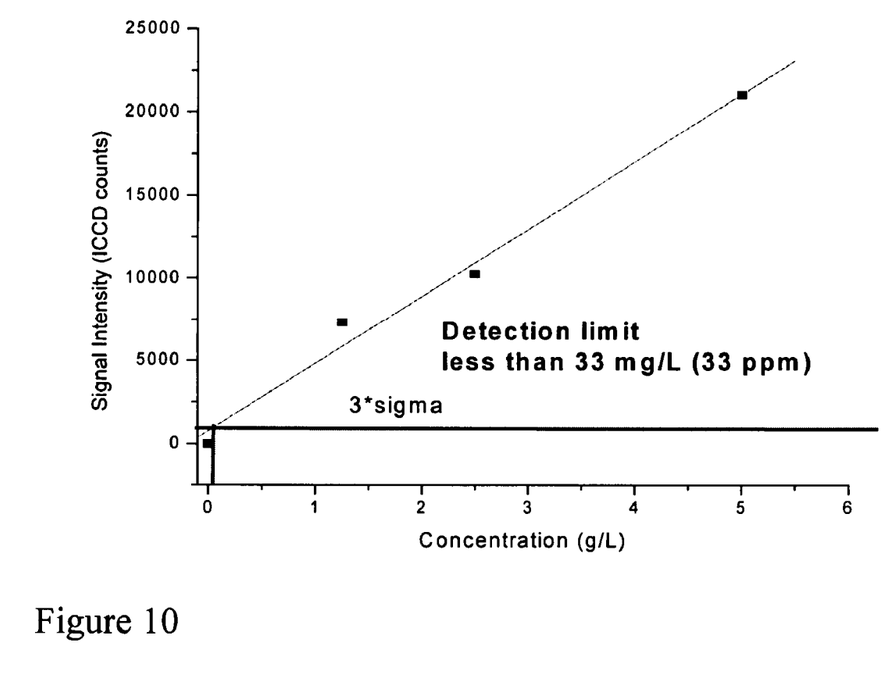
FIG. 10 is a graph showing a sodium signal intensity as a function of sodium chloride concentration for an aerosol cloud located at 50 m from the LIDAR mirror.

To measure the detection limit, the mobile chamber was positioned 50 m away from the LIDAR. The salt concentration was gradually decreased. The linear behavior (FIG. 10) allows the determination of the 3σ detection limit. It was found that, at 50 m, the limit is around 33 ppm. This result demonstrates the great potential of the technique for long distance trace measurements in aqueous aerosols. In FIG. 10, the droplet concentration is 1000 $cm^{-3}$, and the 10 ps negatively chirped pulses have 72 mJ energy.

A sodium fluorescence signal measured at 50 m is used to extrapolate the detection over distance. The following are the experimental conditions: salt concentration, 1.25 g/L; filament length, 1.5 m and 1000 laser shots accumulation. The LIDAR equation $I \sim LIR^2$ (where I is the signal intensity, L the effective filament length and R the distance between the end of the filament and the detector) is used to extrapolate this result over distance. We estimate that, for a filament length of L=20 m, the signal detection limit of 3 standard deviations will be reached, with 10000 shots accumulation, slightly beyond 1.25 km. However, to achieve this kilometer range detection limit requires control over the onset of the filaments. As previously mentioned, this obstacle could be circumvented using the current device. Since the closest clouds, Cumulus humilis, are located around 500-1000 m over sea level, this result opens a way for efficient ppm level remote sensing of atmospheric aerosols in air.

In short, we prove that the nonlinear fluorescence spectra from different kinds of molecules interacting with intense femtosecond laser field constitute the distinct evidence of fingerprints of pollutants, and sub-ppm (part per million) level of detection sensitivity can be achieved. The proposed technique is based upon the most advanced modern femtosecond laser technology; it is unique and powerful in the sense that one laser would be able to sense all molecular pollutants simultaneously. No other type of laser could do so. The application of this technique could lead to the establishment and enhancement of activities in photonics industries and government organizations interested in atmospheric pollution monitoring. In particular, this technique can be applied to monitoring chemical/biological pollutants in the atmosphere spread over by terrorist groups.

Figure 5:
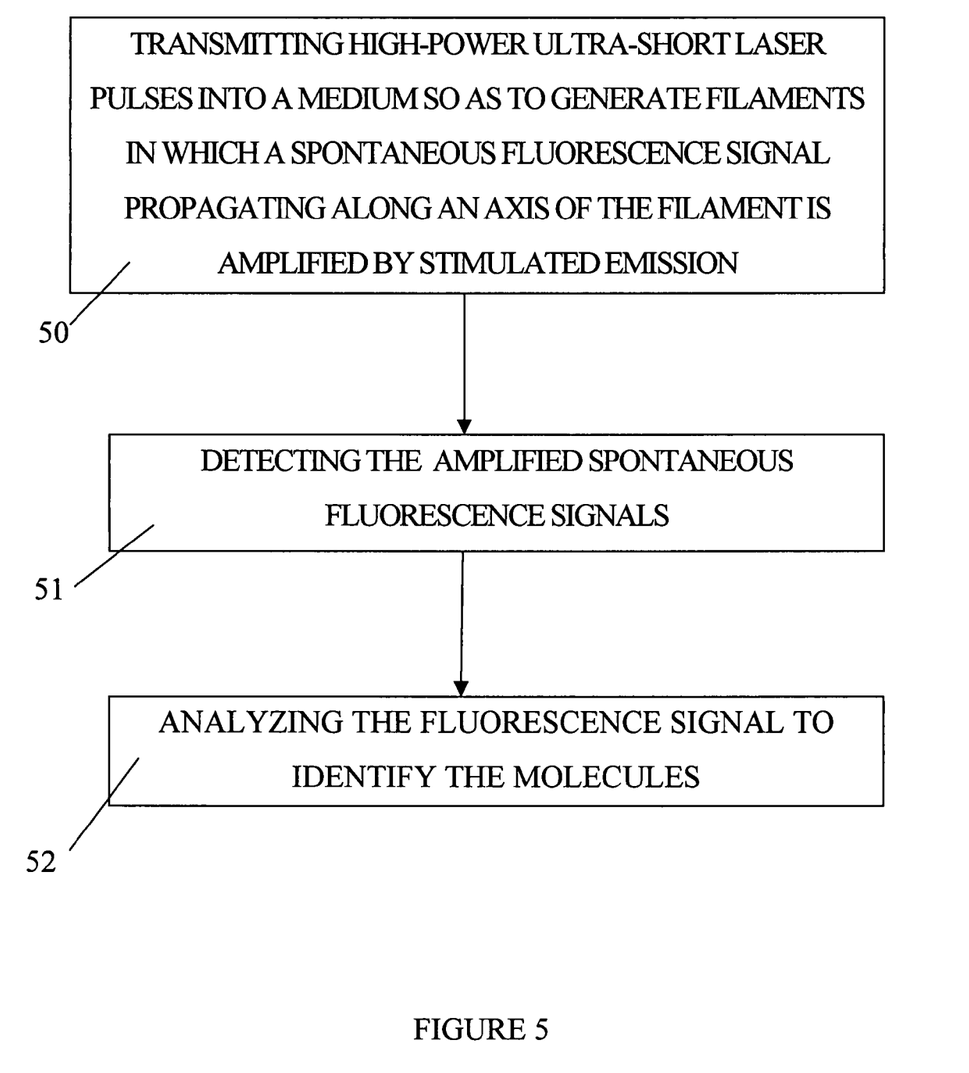
FIG. 5 is a flow chart of the method according to an embodiment of the invention.

FIG. 5 is a flowchart showing the method according to an embodiment of the present invention. The first step is to transmit a high-power, ultra-short laser pulse into a transparent medium so as to generate filaments in which a spontaneous fluorescence signal propagating along the axis of said filament is amplified by stimulated emission 50. When transmitting femtosecond laser pulses into the atmosphere, or any other substantially transparent medium, a weak plasma column is formed and serves as an amplifying waveguide to the spontaneous emission fluorescence signals. The amplified spontaneous fluorescence signals are then detected 51 and analyzed to identify molecules from the unique characteristics in their fluorescence spectrum 52.

Preferably, the transmitting is done using a femtosecond laser, and more specifically, a terawaft femtosecond Ti:sapphire laser system. Also preferably, the detected signals are in a direction opposite that of the transmitted pulse and received by the detector, which is placed at the same location as the source. As an additional feature, a trigger-and-delay electronics device is present in order to capture signals from a certain distance from the source and the detector is gated. For example, when the medium of transmission is air, the time at which the fluorescence spectra are acquired determines at what height the detection is being done. The longer the delay between the laser pulse and the acquisition of the spectrum, the higher the signal is coming from. The transmission medium can be air, water, or any other medium that is substantially transparent and in which a filament can be formed.

Figure 6:
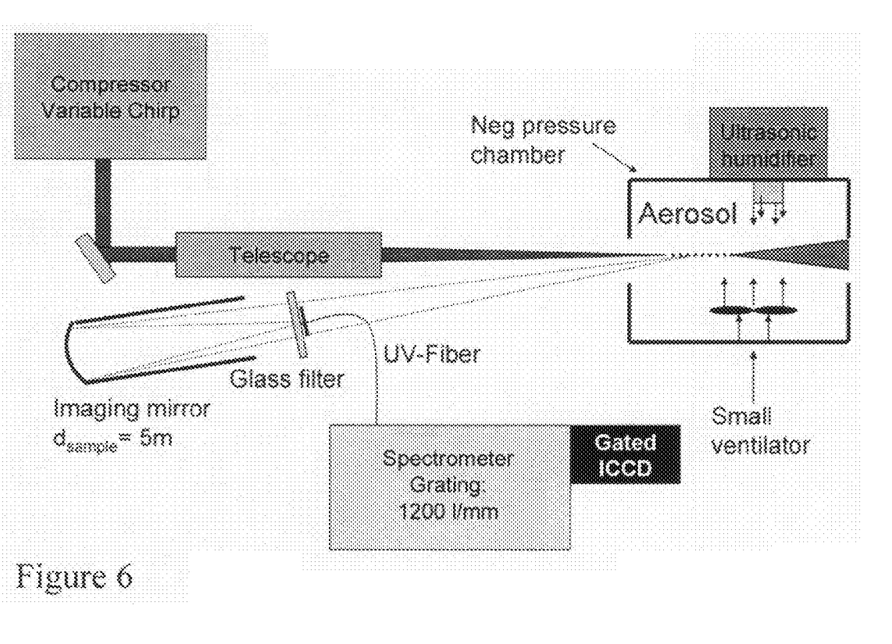
FIG. 6 illustrates an experimental setup for spectral characterization of aerosols.
Figure 7:
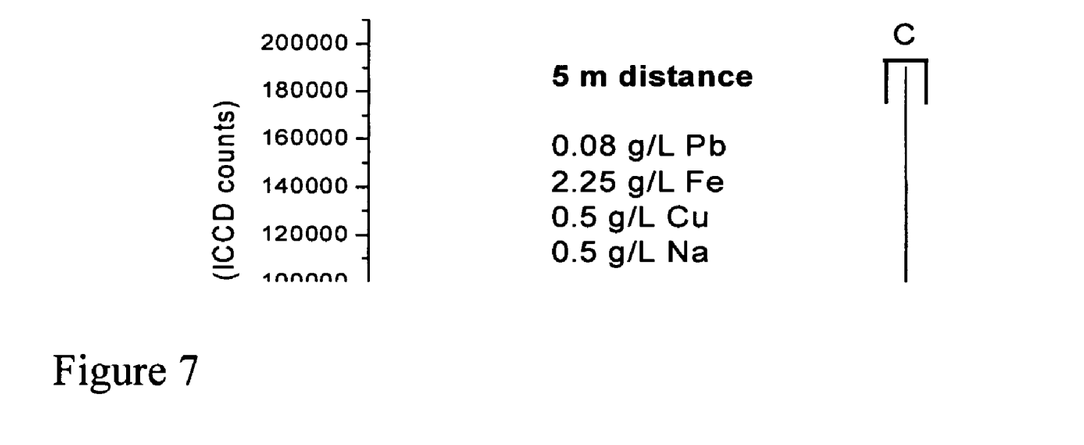
FIG. 7 is a graph of a typical filament-induced spectrum in a thin aerosol cloud characterized with a 95% transmission of the 632 nm wavelength.
Figure 8A:
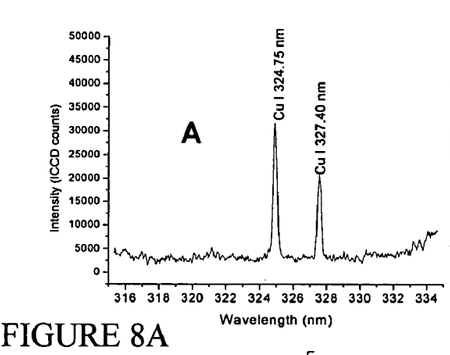
FIGS. 8a, 8b, and 8c are graphs of the regions referred to as A, B and C in FIG. 7. A corresponds to Cu I, B corresponds to Fe I and Pb I and C corresponds to Na I.
Figure 8B:
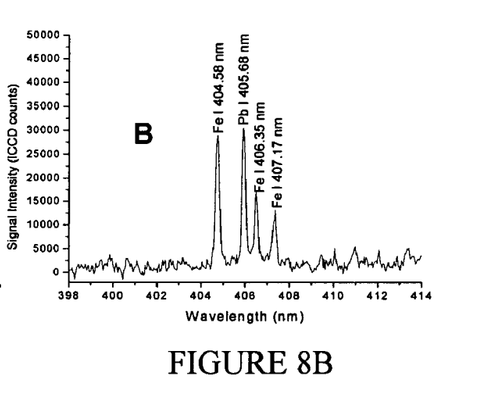
Figure 8C:
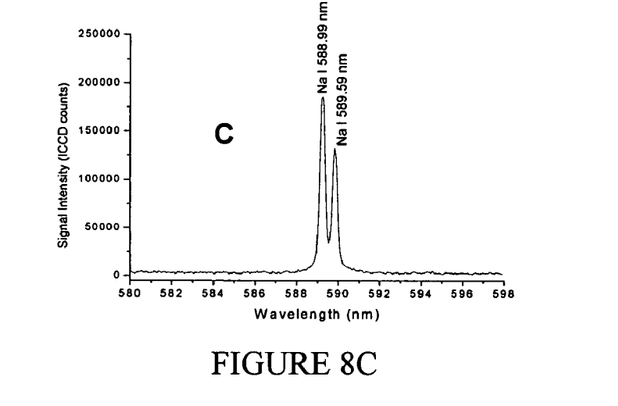
Figure 9:
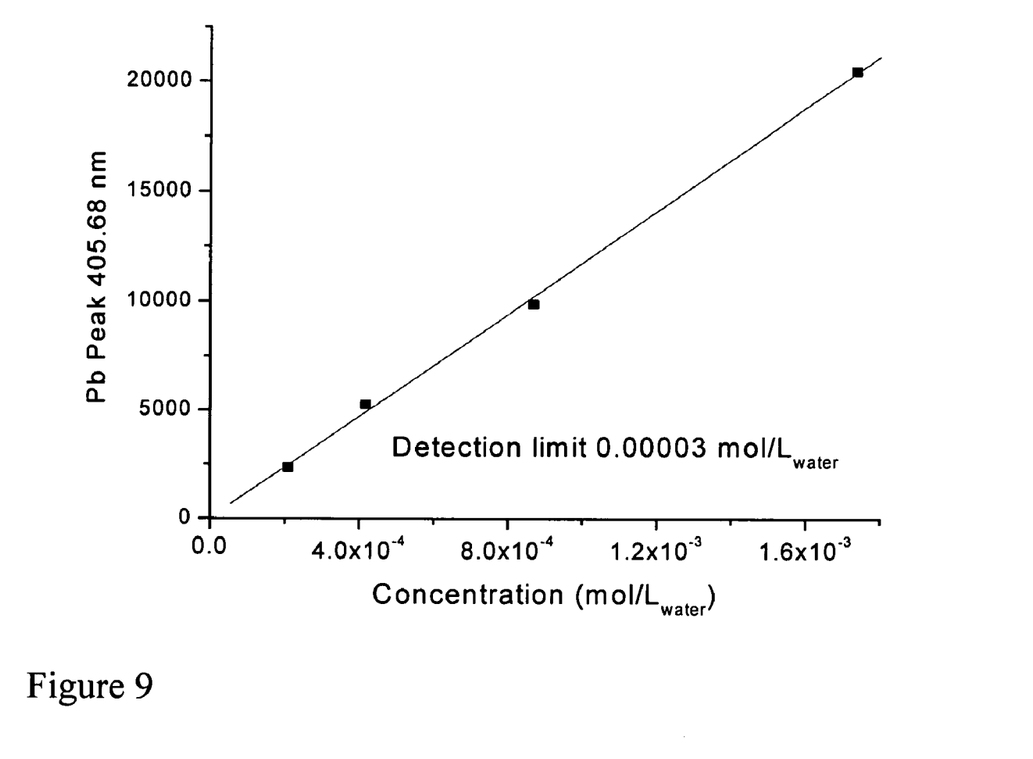
FIG. 9 is a graph showing lead signal intensity as a function of lead dichloride concentration for an aerosol cloud located at 5 m from the LIDAR mirror.

It will be understood that numerous modifications thereto will appear to those skilled in the art. Accordingly, the above description and accompanying drawings should be taken as illustrative of the invention and not in a limiting sense. For example, it is not necessary to detect the signal along the propagation axis. One could detect the back or forward directed signals from an angle as illustrated in FIG. 6 to detect the scattered fluorescence with no amplification. Another example is that one or more optical elements including electronically controlled adaptive optical elements such as deformable mirrors could be added to or used as optical elements of the current optical device so as to modify the properties of the individual hot zones of the laser pulse. This would enhance the modification of the self-focusing distance. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

The invention claimed is:

1. A method for identifying at least one target in a substantially transparent medium, the method comprising:
    transmitting high-power, ultra-short laser pulses into the medium, enlarging a diameter of said laser pulses, and focusing said laser pulses having an enlarged beam diameter using a focusing element so as to generate filaments substantially near a geometrical focal zone of the focusing element;
    detecting a spontaneous fluorescence signal; and
    analyzing said florescence signal to identify said target.

2. A method as claimed in claim 1, further comprising providing a variable effective focal length for said focusing element.

3. A method as claimed in claim 1, wherein said providing a variable effective focal length comprises providing said focusing element on a motorized stage.

4. A method as claimed in claim 1, wherein said enlarging a diameter of said laser pulses comprises using a convex mirror for said enlarging.

5. A method as claimed in claim 1, wherein said enlarging a diameter of said laser pulses comprises using a concave lens for said enlarging.

6. A method as claimed in claim 1, wherein said at least one target is a constituent of aerosol.

7. A method as claimed in claim 6, wherein said analyzing comprises a qualitative and quantitative analysis of said at least one target in aerosol.

8. A method as claimed in claim 1, wherein said at least one target is a gaseous molecule in the atmosphere.

9. A method as claimed in claim 1, wherein said at least one target is a solid molecule in the atmosphere.

10. A method as claimed in claim 1, wherein said spontaneous fluorescence is amplified by stimulated emission.

11. A system for remote detection of at least one target in a substantially transparent medium, the system comprising:
    a laser system for transmitting high-power, ultra-short laser pulses into the medium;
    an optical element for enlarging a beam diameter of said laser pulses;
    a focusing element for focusing said laser pulses having an enlarged beam diameter so as to generate filaments substantially near a geometrical focal zone of the focusing element; and
    a detection system for detecting a spontaneous fluorescence signal in one of a forward and a backward direction.

12. A system as claimed in claim 11, wherein said laser system is a terawatt femtosecond Ti-sapphire laser system.

13. A system as claimed in claim 11, wherein said optical element is a convex mirror.

14. A system as claimed in claim 11, wherein said optical element is a concave lens.

15. A system as claimed in claim 11, wherein said focusing element is a lens.

16. A system as claimed in claim 15, wherein said lens is on a motorized stage to provide a variable effective focal length.

17. A system as claimed in claim 11, wherein said detection system comprises a Light Detecting and Ranging (LIDAR) system, a spectrometer, a photomultiplier tube or a CCD detector or an ICCD detector and an oscilloscope coupled to a computer.

18. A system as claimed in claim 11, wherein said detection system comprises a shutter set to open after a predetermined period of time.

19. A system as in claimed 11, wherein said optical element comprises electronically controlled deformable mirrors.

* * * * *